United States Patent [19]

Montzka

[11] 4,440,933
[45] Apr. 3, 1984

[54] PROCESS FOR PREPARING 1,2,5-THIADIAZOLES

[75] Inventor: Thomas A. Montzka, Manlius, N.Y.

[73] Assignee: Bristol-Myers Company, New York, N.Y.

[21] Appl. No.: 475,985

[22] Filed: Mar. 16, 1983

[51] Int. Cl.$^3$ ........................................... C07D 285/10
[52] U.S. Cl. ..................... 546/193; 546/209; 546/256; 546/277; 548/134; 548/135; 548/127; 544/60; 544/124; 544/134; 544/360; 544/364; 544/367; 260/245.5
[58] Field of Search ................. 544/60, 134, 124, 360, 544/367, 364; 546/193, 194, 209, 256, 277; 548/127, 134, 135; 260/245.5

[56] References Cited

U.S. PATENT DOCUMENTS

| | | | |
|---|---|---|---|
| 4,374,248 | 2/1983 | Crenshaw et al. | 548/135 |
| 4,380,638 | 4/1983 | Crenshaw et al. | 546/193 |
| 4,380,639 | 4/1983 | Crenshaw et al. | 546/193 |
| 4,394,508 | 7/1983 | Crenshaw et al. | 546/209 |

FOREIGN PATENT DOCUMENTS 40696  12/1981  European Pat. Off. ............ 548/135

OTHER PUBLICATIONS

Harpp et al., "Tetrahedron Letters", No. 15, pp. 1481–1484, (1972).
Weinstock et al., "J. Organic Chem.", vol. 32, pp. 2823–2829, (1967).
Kalnins, "Canadian J. Chem.", vol. 44, pp. 2111–2113, (1966).
Harpp et al., "J. Am. Chem. Soc.", vol. 100, pp. 1222–1228, (1978).
Sosnovsky et al., "Liebig's Ann der Chemie", pp. 121–136, (1982).

Primary Examiner—Robert T. Bond
Attorney, Agent, or Firm—Richard R. Lloyd

[57] ABSTRACT

Histamine $H_2$-receptor antagonists of the formula

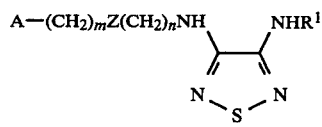

I wherein A, m, Z, n and $R^1$ are as defined herein, and their nontoxic pharmaceutically acceptable salts, hydrates and solvates are novel anti-ulcer agents which are prepared by ring closure of a substituted ethanediimidamide of the formula

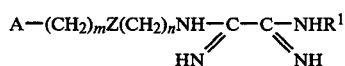

II with a compound of the formula

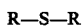

in which R is as defined herein.

9 Claims, No Drawings

PROCESS FOR PREPARING 1,2,5-THIADIAZOLES

SUMMARY OF THE INVENTION

Process for the preparation of certain 3-(amino or substituted amino)-4-(substituted amino)-1,2,5-thiadiazole histamine $H_2$-antagonists of the formula

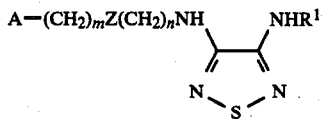

wherein A, m, Z, n and $R^1$ are as defined below, and their nontoxic pharmaceutically acceptable salts, hydrates and solvates, which comprises reacting a correspondingly substituted ethanediimidamide of the formula

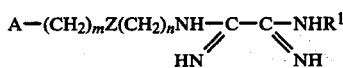

with a compound of the formula

     VII in which the two R groups are the same and may be

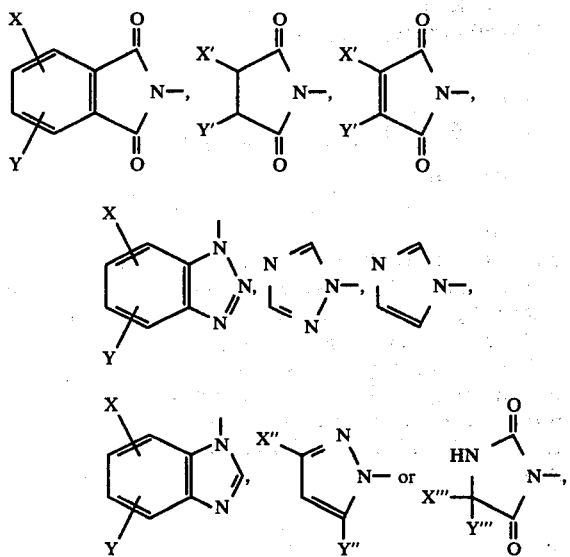

in which X and Y are independently hydrogen, (lower)alkyl, (lower)alkoxy, chloro, bromo, nitro, methanesulfonyl, benzenesulfonyl, cyclo(lower)alkyl or phenyl, X' and Y' are independently hydrogen, (lower)alkyl or phenyl, X'' and Y'' are independently hydrogen or (lower)alkyl and X''' and Y''' are independently (lower)alkyl or phenyl.

INFORMATION DISCLOSURE STATEMENT

U.S. Pat. No. 4,374,248 (R. R. Crenshaw and A. A. Algieri), issued Feb. 15, 1983, discloses 3,4-disubstituted-1,2,5-thiadiazole-1-oxides and 1,1-dioxides having the formula

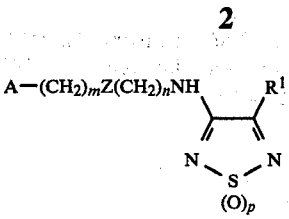

and processes for their preparation, wherein the variables A, m, Z, n and $R^1$ are similar to the corresponding substituents of the compounds of Formula I prepared by the process of the present invention. However, the compounds disclosed therein are 1-oxides or 1,1-dioxides (p is 1 or 2), and the compounds of Formula I herein cannot be prepared by any of the processes described therein for the preparation of the prior art compounds.

European Patent Application No. 40,696, published Dec. 2, 1981, discloses inter alia 3,4-disubstituted-1,2,5-thiadiazole 1-oxides and 1,1-dioxides having the formula

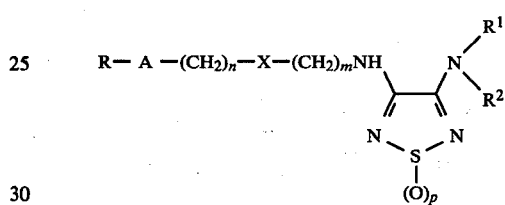

and processes for their preparation, wherein the variables R, Ⓐ, n, X, m, $R^1$ and $R^2$ are similar to the corresponding substituents of the compounds of Formula I prepared by the process of the present invention. However, the compounds disclosed therein also are 1-oxides or 1,1-dioxides (p is 1 or 2) and the compounds of Formula I herein cannot be prepared by any of the processes described therein for the preparation of the prior art compounds.

In Tetrahedron Letters, No. 15, 1481–4 (1972), D. N. Harpp and T. G. Back disclose the use of N,N'-thiobisphthalimide (hereinafter N,N'-TBP) for cyclizing secondary ethane- and 1,3-propanediamines, to the corresponding 1,2,5-thiadiazolidine or 1,2,6-perhydrothiadiazine, as follows:

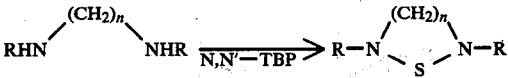

where n=2 and R=methyl or n=3 and R=ethyl.

In J. Organic Chem., 32, 2823–9 (1967), L. M. Weinstock et al. describe the preparation of simple 3-substituted or 3,4-disubstituted 1,2,5-thiadiazoles by ring closure of various acyclic compounds with sulfur monochloride or sulfur dichloride, including the preparation of 3-amino-1,2,5-thiadiazole by the reaction of α-aminoacetamidine dihydrobromide with sulfur monochloride.

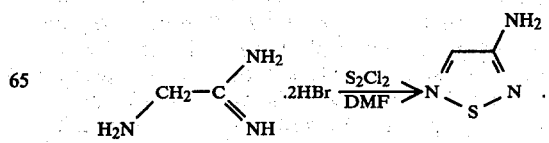

In the Canadian Journal of Chemistry, 44, 2111–2113 (1966), M. V. Kalnins describes the preparation of N,N'-TBP via the following reaction

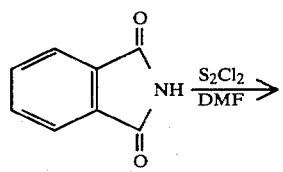

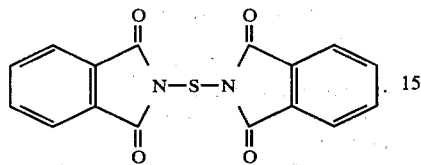

In the Journal of the American Chemical Society, 100, 1222–8 (1978) D. N. Harpp et al. describe the preparation of compounds of the formula R—S—R in which R is

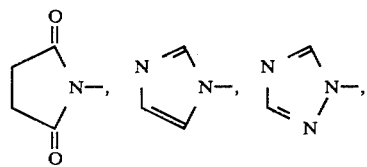

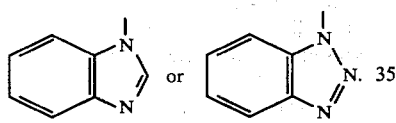

The compounds were prepared by reaction of sulfur monochloride or sulfur dichloride with a trimethylsilyl derivative of the appropriate nitrogen heterocycle.

In Liebigs Ann. Chem., 121–136 (1982), G. Sosnovsky and J. A. Krogh describe the preparation of N,N'-thiobis(5,5-dimethylhydantoin) having the formula

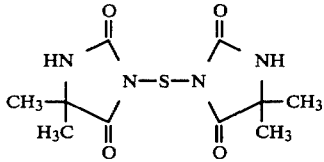

by the reaction of 5,5-dimethylhydantoin with sulfur dichloride.

In U.S. Pat. No. 4,374,248 and published European Application No. 40,696 cited above, the processes described for the preparation of the prior art compounds involve the use (as a starting material or intermediate) of a 1,2,5-thiadiazole 1-oxide or 1,1-dioxide having either amino groups or suitable "leaving groups" on the 3- and 4-positions. The desired substituents on the 3- and 4-positions are then obtained by substitution on the amino groups or by replacement of the "leaving groups". Extensive attempts have been made to prepare the compounds of Formula I herein by similar procedures, i.e. by utilizing 1,2,5-thiadiazole having amino groups or suitable "leaving groups" on the 3- and 4- positions as starting materials or intermediates. Although numerous variations were tried, along with varying reaction conditions, compounds of Formula I herein could not be obtained via that route.

In their co-pending U.S. patent application Ser. No. 363,207, filed Mar. 29, 1982, now abandoned, my colleagues, R. R. Crenshaw and A. A. Algieri, disclose compounds of Formula I herein and the process for their preparation which comprises ring closure of the correspondingly substituted ethanediimidamide of the formula

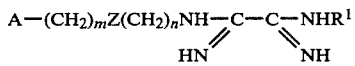

with sulfur monochloride or sulfur dichloride. However, the yields by that route were low (approximately 5–30%) and separation of the desired product from the reaction mixture was tedious.

COMPLETE DISCLOSURE

This invention relates to a process for the preparation of histamine $H_2$-antagonists of the formula

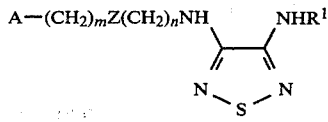

wherein $R^1$ is hydrogen, (lower)alkyl, 2-fluoroethyl, 2,2,2-trifluoroethyl, allyl, propargyl,

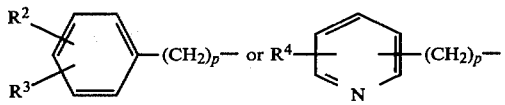

in which
p is 1 or 2, $R^2$ and $R^3$ each are independently hydrogen, (lower)alkyl, (lower)alkoxy or halogen, and, when $R^2$ is hydrogen, $R^3$ also may be trifluoromethyl, or $R^2$ and $R^3$, taken together, may be methylenedioxy, and $R^4$ is hydrogen, (lower)alkyl or (lower)alkoxy;
m is an integer of from 0 to 2 inclusive;
n is an integer of from 2 to 5 inclusive;
Z is oxygen, sulfur or methylene; and
A is

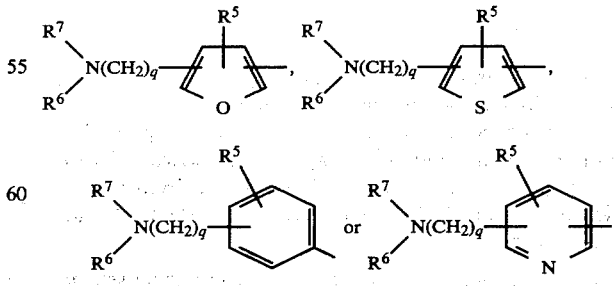

in which $R^5$ is hydrogen, (lower)alkyl or (lower)alkoxy, q is an integer of from 1 to 4 inclusive and $R^6$ and $R^7$ each are independently (lower)alkyl, (lower)alkoxy(lower)alkyl in which the (lower)alkoxy moiety is at least two carbon atoms removed from the nitrogen atom, or phenyl(lower)alkyl, and, when R[6] is hydrogen, R[7] also may be cyclo(lower)alkyl, or R[6] and R[7], taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, 3-azabicyclo[3.2.2]non-3-yl or 3-pyrrolino; and nontoxic, pharmaceutically acceptable salts, hydrates and solvates thereof; which process comprises reacting a correspondingly substituted ethanediimidamide of the formula

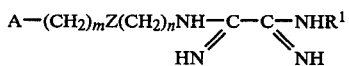   II with a compound of the formula

   VII in which the two R groups are the same and may be

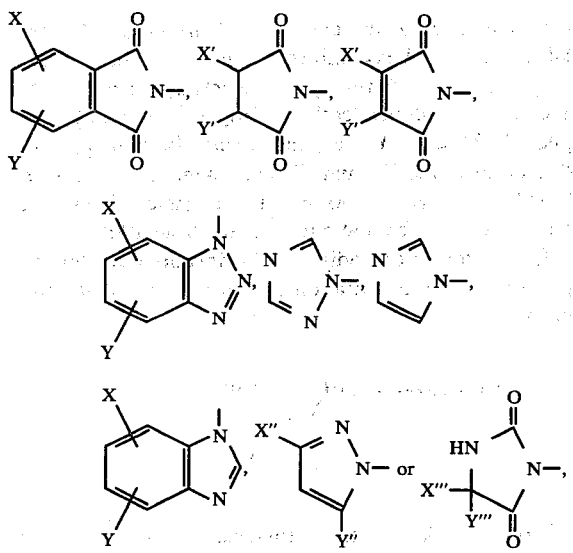

in which X and Y are independently hydrogen, (lower)alkyl, (lower)alkoxy, chloro, bromo, nitro, methanesulfonyl, benzenesulfonyl, cyclo(lower)alkyl or phenyl, X' and Y' are independently hydrogen, (lower)alkyl or phenyl, X'' and Y'' are independently hydrogen or (lower)alkyl and X''' and Y''' are independently (lower)alkyl or phenyl, in a non-reactive organic solvent, at a temperature of from about 0° C. to about 100° C.

In the compounds of Formula I, R[1] preferably is hydrogen or (lower)alkyl, more preferably is hydrogen or methyl and most preferably is hydrogen. Substituent A preferably is the substituted phenyl moiety, substituted furyl moiety or substituted thienyl moiety shown above, and most preferably is the substituted phenyl moiety. Substituent Z preferably is sulfur or oxygen and, when A is the substituted phenyl moiety, Z preferably is oxygen. It is preferred that m is zero or 1 and n is 2 or 3, and that, when A is the substituted phenyl moiety, m is zero and n is 3. R[5] preferably is hydrogen or methyl and most preferably is hydrogen. It is preferred that q is 1. R[6] and R[7] preferably are (lower)alkyl, or, taken together with the nitrogen atom to which they are attached, are pyrrolidino or piperidino.

In reacting a compound of Formula II with a sulfur compound of Formula VII, the reaction ratio is not critical. It is preferred to use at least an equimolar amount of the compound of Formula VII, but an excess may be utilized. It is most preferred to conduct the reaction with about an equimolar amount of Compounds II and VII. The reaction temperature is not critical. At lower temperatures the reaction is slow, while at higher temperatures the production of side products is increased. The preferred reaction temperature is in the range of from about 10° C. to about 50° C., but it is most convenient to conduct the reaction at ambient temperature. The reaction time is not critical, and is dependent on reaction temperature. I normally utilize a reaction time of from about twenty minutes to about three hours. At ambient temperature, a reaction time of about one hour is convenient and usually is sufficient to complete the reaction. The phthalimide which precipitates from the reaction mixture may then be extracted with a strong base (e.g. 10-20% aqueous KOH), and the organic solvent layer is dried, filtered and concentrated to yield the crude compound of Formula I.

The reaction is conducted in a non-reactive organic solvent such as methylene chloride, chloroform, carbon tetrachloride, dimethylformamide, dimethylacetamide, tetrahydrofuran, diglyme, benzene, toluene, xylene or the like.

The compounds of Formula II utilized as starting materials in the process of this invention normally are isolated and stored as an acid addition salt, e.g. a trihydrochloride. Although the acid addition salt can be separately converted to its free base prior to reaction with the sulfur compound of Formula VII, it is not necessary or desirable to do so. This preferably is done in situ simply by adding an appropriate amount of an organic base to a solution of the compound of Formula II prior to reaction with the compound of Formula VII. Thus, for example, when utilizing 1 mole of a compound of Formula II as its trihydrochloride, one should add three moles of a suitable organic base. Suitable organic bases include tertiary amines such as trimethylamine, triethylamine, tri-n-propylamine, triisopropylamine, tri-n-butylamine, pyridine, N-methylmorpholine, N-methylpiperidine, 1,4-diazabicyclo[2.2.2]octane ("DABCO"), 1,8-diazabicyclo[5.4.0]undec-7-ene ("DBU"), 1,5-diazabicyclo[4.3.0]non-5-ene ("DBN") and the like.

The compounds of Formula VII are either known compounds or may be readily prepared by known procedures, e.g. as described in references cited in the "Information Disclosure Statement", above. In the compounds of Formula VII it is most convenient to prepare and utilize those in which X and Y are hydrogen and X' and Y' are methyl. The most preferred compound of Formula VII is N,N'-thiobisphthalimide having the formula

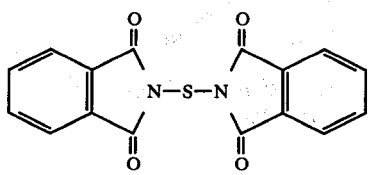

The present invention provides a process for the preparation of a compound of the formula

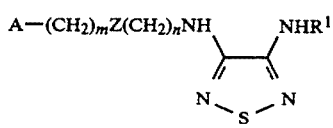

wherein $R^1$ is hydrogen, (lower)alkyl, 2-fluoroethyl, 2,2,2-trifluoroethyl, allyl, propargyl,

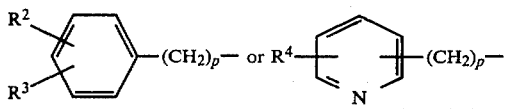

in which
p is 1 or 2, $R^2$ and $R^3$ each are independently hydrogen, (lower)alkyl, (lower)alkoxy or halogen, and, when $R^2$ is hydrogen, $R^3$ also may be trifluoromethyl, or $R^2$ and $R^3$, taken together, may be methylenedioxy, and $R^4$ is hydrogen, (lower)alkyl or (lower)alkoxy;
m is an integer of from 0 to 2 inclusive;
n is an integer of from 2 to 5 inclusive;
Z is oxygen, sulfur or methylene; and
A is

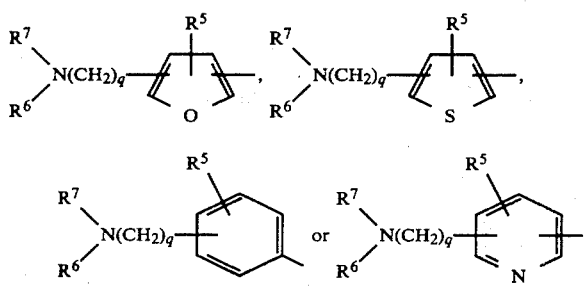

in which $R^5$ is hydrogen, (lower)alkyl or (lower)alkoxy, q is an integer of from 1 to 4 inclusive and $R^6$ and $R^7$ each are independently (lower)alkyl, (lower)alkoxy(lower)alkyl in which the (lower)alkoxy moiety is at least two carbon atoms removed from the nitrogen atom, or phenyl(lower)alkyl, and, when $R^6$ is hydrogen, $R^7$ also may be cyclo(lower)alkyl, or $R^6$ and $R^7$, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, 3-azabicyclo[3.2.2]non-3-yl or 3-pyrrolino; and nontoxic, pharmaceutically acceptable salts, hydrates and solvates thereof; which process comprises reacting a substituted ethanediimidamide of the formula $$A-(CH_2)_mZ(CH_2)_nNH-C-C-NHR^1, \quad II$$
$$\phantom{A-(CH_2)_mZ(CH_2)_nNH-}\underset{HN}{\parallel}\phantom{-}\underset{NH}{\parallel}$$

in which A, m, Z, n and $R^1$ are as described above, with a compound of the formula

R—S—R  VII in which the two R groups are the same and may be

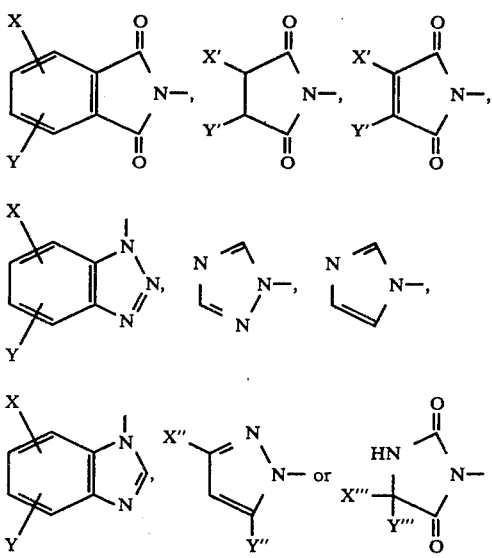

in which X and Y are independently hydrogen, (lower)alkyl, (lower)alkoxy, chloro, bromo, nitro, methanesulfonyl, benzenesulfonyl, cyclo(lower)alkyl or phenyl, X' and Y' are independently hydrogen, (lower)alkyl or phenyl, X" and Y" are independently hydrogen or (lower)alkyl and X''' and Y''' are independently (lower)alkyl or phenyl, in a non-reactive organic solvent, at a temperature of from about 0° C. to about 100° C.

In a preferred embodiment, this invention relates to a process for the preparation of a compound of the formula

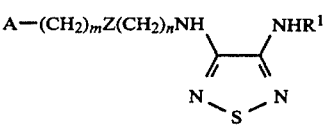

wherein $R^1$ is hydrogen or (lower)alkyl, m is 0 or 1, n is 2 or 3, Z is oxygen or sulfur and A is

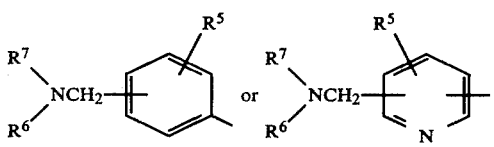

in which $R^5$ is hydrogen or methyl, and $R^6$ and $R^7$ each are independently methyl or ethyl, or when taken together with the nitrogen to which they are attached, $R^6$ and $R^7$ represent a pyrrolidino or piperidino ring; or a nontoxic pharmaceutically acceptable salt, hydrate or solvate thereof; which process comprises reacting a substituted ethanediimidamide of the formula

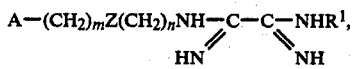

in which A, m, Z, n and $R^1$ are as described above, with a compound of the formula

R—S—R  VII in which the two R groups are the same and may be

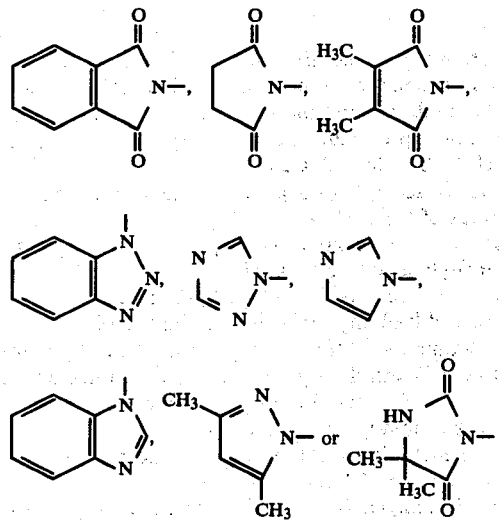

in a non-reactive organic solvent, at a temperature of from about 0° C. to about 100° C.

In a more preferred embodiment, this invention relates to a process for the preparation of a compound of the formula

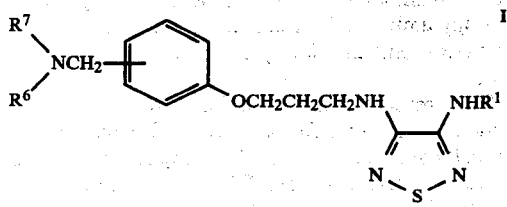

wherein $R^1$ is hydrogen or methyl, and $R^6$ and $R^7$ each are methyl or, when taken together with the nitrogen atom to which they are attached, $R^6$ and $R^7$ represent a pyrrolidino or piperidino ring; or a nontoxic pharmaceutically acceptable salt, hydrate or solvate thereof; which process comprises reacting a compound of the formula

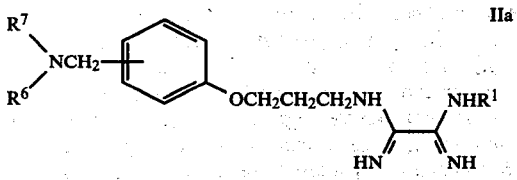

in which $R^1$, $R^6$ and $R^7$ are as defined above, with N,N'-thiobisphthalimide in a non-reactive organic solvent at a temperature of from about 10° C. to about 50° C.

In another more preferred embodiment, this invention relates to a process for the preparation of a compound of the formula

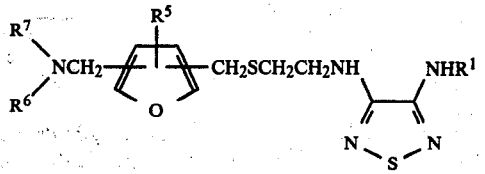

wherein $R^1$ and $R^5$ each are independently hydrogen or methyl, and $R^6$ and $R^7$ each are independently methyl or ethyl; or a nontoxic pharmaceutically acceptable salt, hydrate or solvate thereof; which process comprises reacting a compound of the formula

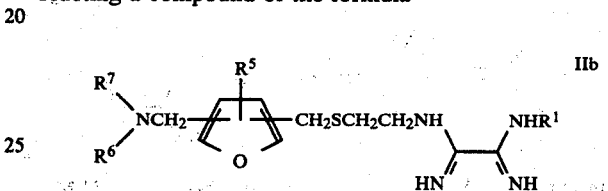

in which $R^1$, $R^5$, $R^6$ and $R^7$ are as defined above, with N,N'-thiobisphthalimide in a non-reactive organic solvent at a temperature of from about 10° C. to about 50° C.

In another more preferred embodiment, this invention relates to a process for the preparation of a compound of the formula

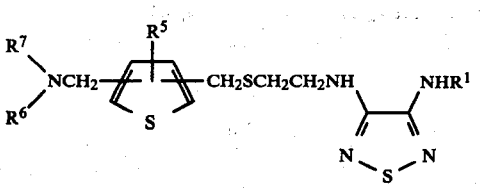

wherein $R^1$ and $R^5$ each are independently hydrogen or methyl, and $R^6$ and $R^7$ each are independently methyl or ethyl; or a nontoxic pharmaceutically acceptable salt, hydrate or solvate thereof; which process comprises reacting a compound of the formula

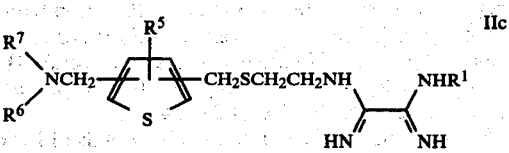

in which $R^1$, $R^5$, $R^6$ and $R^7$ are as defined above, with N,N'-thiobisphthalimide in a non-reactive organic solvent at a temperature of from about 10° C. to about 50° C.

In another more preferred embodiment, this invention relates to a process for the preparation of a compound of the formula

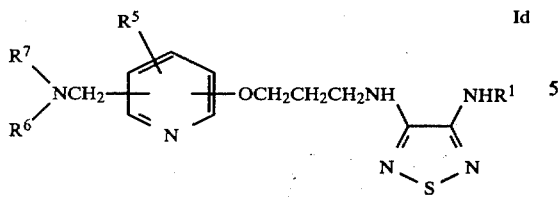

wherein $R^1$ and $R^5$ each are independently hydrogen or methyl, and $R^6$ and $R^7$ each are independently methyl or ethyl, or, when taken together with the nitrogen to which they are attached, $R^6$ and $R^7$ represent piperidino; or a nontoxic pharmaceutically acceptable salt, hydrate or solvate thereof; which process comprises reacting a compound of the formula

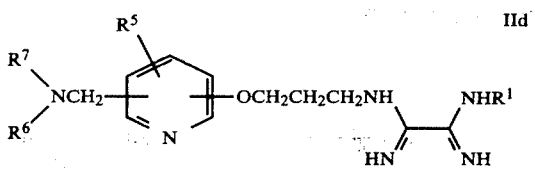

in which $R^1$, $R^6$ and $R^7$ are as defined above, with N,N'-thiobisphthalimide in a non-reactive organic solvent at a temperature of from about 10° C. to about 50° C.

The intermediates of Formula II used in the preparation of the compounds of Formula I may themselves be prepared by various procedures. In one procedure, the corresponding 3-(amino or substituted amino)-4-(substituted amino)-1,2,5-thiadiazole 1-oxide of Formula III is treated with a strong mineral acid (preferably HCl) to produce the compound of Formula II.

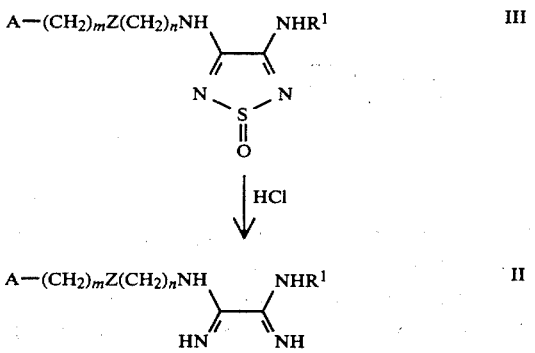

The reaction may be conducted in an inert solvent and preferably is conducted in methanol. Reaction temperature is not critical; it most conveniently is conducted at room temperature. The compounds of Formula III are known or may readily be prepared by the procedures described in U.S. Pat. No. 4,374,248.

In an alternate procedure, the compounds of Formula II may be prepared by the following reaction scheme. The

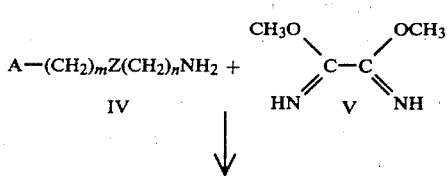

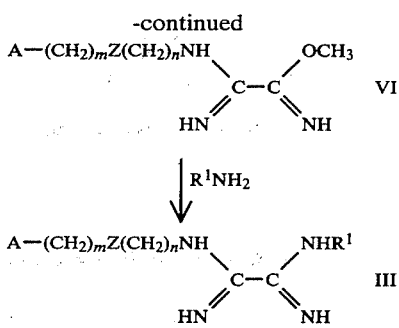

reaction may be conducted in an inert solvent and preferably is conducted in methanol. The starting materials of Formula IV are known or may be readily prepared by known procedures, e.g. as by procedures described in U.S. Pat. No. 4,374,248.

As presently envisaged, the most preferred compounds of Formula I are (1) 3-amino-4-[3-(3-piperidinomethylphenoxy)-propylamino]-1,2,5-thiadiazole, (2) 3-amino-4-{2-[(5-dimethylaminomethyl-2-furyl)-methylthio]ethylamino}-1,2,5-thiadiazole;

(3) 3-amino-4-{2-[(5-dimethylaminomethyl-4-methyl-2-thienyl)methylthio]ethylamino}-1,2,5-thiadiazole, (4) 3-amino-4-[3-(3-pyrrolidinomethylphenoxy)-propylamino]-1,2,5-thiadiazole, (5) 3-methylamino-4-[3-(3-piperidinomethylphenoxy)-propylamino]-1,2,5-thiadiazole, (6) 3-benzylamino-4-[3-(3-piperidinomethylphenoxy)-propylamino]-1,2,5-thiadiazole, (7) 3-amino-4-{2-[(5-dimethylaminomethyl-3-thienyl)-methylthio]ethylamino}-1,2,5-thiadiazole, (8) 3-amino-4-{2-[(5-piperidinomethyl-3-thienyl)-methylthio]ethylamino}-1,2,5-thiadiazole, (9) 3-amino-4-[3-(6-piperidinomethyl-2-pyridyloxy)-propylamino]-1,2,5-thiadiazole and

(10) 3-amino-4-[3-(4-piperidinomethyl-2-pyridyloxy)-propylamino]-1,2,5-thiadiazole; and their nontoxic, pharmaceutically acceptable salts, hydrates and solvates.

The present invention includes within its scope all possible tautomeric forms, diastereoisomeric forms and optically active isomers of the compounds of Formula I as well as mixtures thereof. As used herein and in the claims, the term "(lower)alkyl" means a straight or branched chain alkyl group containing from 1 to 6 carbon atoms. The term "(lower)alkoxy" means a straight or branched chain alkoxy group containing from 1 to 4 carbon atoms. "Cyclo(lower)alkoxy" means a cycloalkyl group containing from 3 to 6 carbon atoms. The term "nontoxic pharmaceutically acceptable salts" means acid addition salts formed with acids such as hydrochloric, hydrobromic, nitric, sulfuric, acetic, propionic, fumaric, methanesulfonic, maleic, tartaric, citric, levulinic, benzoic, succinic and the like.

For therapeutic use, the pharmacologically active compounds of Formula I will normally be administered as a pharmaceutical composition comprising as the (or an) essential active ingredient at least one such compound in its basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compounds of Formula I will depend not only on such factors as the weight of the patient, but also on the degree of gastric acid inhibition desired and the potency of the particular compound being utilized. The decision as to the particular dosage to be employed (and the number of times to be administered per day) is within the discretion of the physician, and may be varied by titration of the dosage to the particular circumstances of the specific patient. With the preferred compounds of Formula I, each oral dosage unit will contain the active ingredient in an amount of from about 2 mg to about 300 mg, and most preferably from about 4 mg to about 100 mg. The active ingredient will preferably be administered in equal doses from one to four times a day.

Histamine $H_2$-receptor antagonists have been shown to be effective inhibitors of gastric secretion in animals and man, Brimblecombe et al., J. Int. Med. Res., 3, 86 (1975). Clinical evaluation of the histamine $H_2$-receptor antagonist cimetidine has shown it to be an effective therapeutic agent in the treatment of peptic ulcer disease, Gray et al., Lancet, 1, 8001 (1977). Some of the preferred compounds of Formula I have been compared with cimetidine in various tests and have been found to be more potent than cimetidine both as an histamine $H_2$-receptor antagonist in isolated guinea pig right atria and as an inhibitor of gastric acid secretion in rats and dogs.

DETERMINATION OF GASTRIC ANTISECRETORY ACTIVITY IN THE GASTRIC FISTULA RAT

Male Long Evans rats weighing about 240–260 grams at the time of cannula implantation are used. The design and implantation of the stainless steel cannula into the anterior wall of the fore-stomach are carried out essentially as described by Pare et al. [Laboratory Animal Science, 27, 244 (1977)]. The fistula components are designed and the operative procedure is carried out exactly as described in the above reference. Post operatively the animals are individually housed in solid bottom cages with sawdust and are allowed food and water ad libitum throughout the entire recovery period. Animals are not used for test purposes for at least 15 days after the operative procedure.

The animals are fasted but allowed water ad libitum for 20 hours before the testing procedure is to begin. Immediately prior to collection, the cannula is opened and the stomach washed gently with 30–40 mL of warm saline or distilled water to remove any residual contents. The catheter is then screwed into the cannula in place of the plugging screw and the rat is placed in a clear plastic rectangular cage measuring 40 cm long, 15 cm wide and 13 cm high. The bottom of the cage has a slit approximately 1.5 cm wide and 25 cm long running down the center to accommodate the catheter which hangs through it. In this way the rat is not restricted and can move freely about the cage during collection periods. The remainder of the assay is carried out as described by Ridley et al. [Research Comm. Chem. Path. Pharm., 17, 365 (1977)].

Gastric secretions collected during the first hour after washing the stomach are discarded as they may be contaminated. For oral evaluation, the catheter is then removed from the cannula and replaced with the plugging screw. Water (2 mL/kg) is administered orally via gastric intubation and the animal is returned to the cage for 45 minutes. After this time the plugging screw is removed and replaced with a catheter to which a small plastic vial has been attached to collect the gastric secretions. A two-hour sample is collected (this represents the control secretion), the catheter is removed and replaced with the plugging screw. The test drug is now administered orally in a volume of 2 mL/kg via gastric intubation. Forty-five minutes later the plugging screw is again removed, replaced with the catheter attached to a small plastic vial and another 2-hour sample is collected. The secretions in the second sample are compared to those of the control sample in order to determine the effects of the test drug.

When test compounds are to be evaluated parenterally, the animal is injected ip or sc with the test compound vehicle in a volume of 2 mL/kg immediately after discarding the initial 60-minute collection. A two-hour sample is collected (control secretion) and the animals are injected either ip or sc with the test compound in a volume of 2 mL/kg. An additional two-hour sample is collected and its secretions are compared to those of the control period to determine drug effects.

The samples are centrifuged and placed in a graduated centrifuge tube for volume determination. Titratable acidity is measured by titrating a one-mL sample to pH 7.0 with 0.02 N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings. Dose response curves are constructed and $ED_{50}$ values are calculated by regression analyses. At least three rats are used at each dosage level and a minimum of three dosage levels are utilized for determination of a dose response curve.

TABLE 1

| Gastric Antisecretory Activity in the Gastric Fistula Rat | | |
|---|---|---|
| Compound | $ED_{50}$ sc μmoles/kg | Potency Ratio (cimetidine = 1.0) |
| cimetidine | 3.48 (1.68–5.75)* | 1.0 |
| Example 3 | 0.094 (0.043–0.20) | 37 |
| Example 10 | 0.77 (0.45–1.4) | 4.5 |
| Example 11 | ~0.5 | ~7 |
| Example 4 | 0.18 (0.10–0.36) | 20 |

*95% confidence limits

HISTAMINE $H_2$-RECEPTOR ANTAGONISM-ISOLATED GUINEA PIG ATRIA ASSAY

Histamine produces concentration-related increases in the contractile rate of isolated, spontaneously beating guinea pig right atria. Black et al., Nature, 236, 385 (1972), described the receptors involved in this effect of histamine as histamine $H_2$-receptors when they reported the properties of burimamide, a competitive antagonist of these receptors. Subsequent investigations by Hughes and Coret, Proc. Soc. Exp. Biol. Med., 148, 127 (1975) and Verma and McNeill, J. Pharmacol. Exp. Ther., 200, 352 (1977) support the conclusion of Black and coworkers that the positive chronotropic effect of histamine in isolated guinea pig right atria is mediated via histamine $H_2$-receptors. Black et al., Agents and Actions, 3, 133 (1973) and Brimblecombe et al., Fed. Proc., 35, 1931 (1976) have utilized isolated guinea pig right atria as a means for comparing the activities of histamine $H_2$-receptor antagonists. The present comparative studies were carried out using a modification of the procedure reported by Reinhardt et al., Agents and Actions, 4, 217 (1974).

Male Hartley strain guinea pigs (350–450 gm) were sacrificed by a blow on the head. The heart was excised and placed in a Petri dish of oxygenated (95% $O_2$, 5% $CO_2$) modified Krebs solution (g/liter: NaCl 6.6, KCl 0.35, $MgSO_4.7H_2O$ 0.295, $KH_2PO_4$ 0.162, $CaCl_2$ 0.238, $NaHCO_3$ 2.1 and dextrose 2.09). The spontaneously beating right atrium was dissected free from other tissues and a silk thread (4-0) attached to each end. The atrium was suspended in a 20 ml muscle chamber containing oxygenated modified Krebs solution maintained at 32° C. Atrial contractions were recorded isometrically by means of a Grass FT 0.03 force displacement transducer and recordings of contractile force and rate were made with a Beckman RP Dynograph.

A resting tension of 1 g was applied to the atrium and it was allowed to equilibrate for 1 hour. At the end of the equilibration period a submaximal concentration of histamine dihydrochloride ($3 \times 10^{-6}$ M) was added to the bath and washed out to prime the tissue. Histamine was then added to the bath in a cumulative fashion using $\frac{1}{2}$ log 10 intervals to give final molar bath concentrations of $1 \times 10^{-7}$ to $3 \times 10^{-5}$. The histamine-induced increase in atrial rate was allowed to plateau before the next successive concentration was added. The maximal response invariably occurred at the $3 \times 10^{-5}$ M concentration. The histamine was washed out several times and the atrium allowed to return to control rate. The test compound was then added at appropriate molar concentrations and, after a 30-minute incubation, the histamine dose response was repeated adding higher concentrations as needed.

The dissociation constants ($K_B$) were derived from Schild plots by the method of Arunlakshana, O. and Schild, H. O. [Br. J. Pharmacol. 14, 48 (1959)] using at least three dose levels. Parallel shifts in dose-response curves were obtained without depressing the maximal response at the antagonist concentrations utilized, and the results are shown in Table 2.

TABLE 2

| Activity in Isolated Guinea Pig Right Atria | | | |
|---|---|---|---|
| Compound | N | $K_B$ (μmoles) | Potency Ratio (cimetidine = 1.0) |
| cimetidine | 20 | 0.41 (.21–.64)* | 1.0 |
| Example 3 | 12 | 0.003 (.001–.004) | 137 |
| Example 4 | 11 | 0.004 (.001–.010) | 102 |

*95% confidence limits

PREPARATION NO. 1

N,N′-Thiobisphthalimide

A cooled (0° C.) solution of phthalimide (14.7 g, 0.1 mole) in 80 ml of dimethylformamide (DMF) was treated dropwise with sulfur dichloride (5.15 g, 0.05 mole). After the addition, the mixture was allowed to warm to 20° C. with stirring over four hours. The solid was collected and dried to give 12.5 g of the title compound as a DMF solvate, mp 301°–315° C. Both ir and nmr spectra are consistant for structure.

Anal. Calc'd. for $C_{16}H_8N_2O_4S.C_3H_7NO$: C, 57.42; H, 3.80; N, 10.57; S, 8.07. Found: C, 57.50; H, 3.80; N, 10.29; S, 8.57.

The DMF solvate can be removed by recrystallization of the above material from chloroform; mp of the DMF-free product was 320°–325° C. The nmr spectrum shows that the DMF has been removed.

Anal. Calc'd. for $C_{16}H_8N_2O_4S$: C, 59.25; H, 2.49; N, 8.64; S, 9.89. Found: C, 59.21; H, 2.21; N, 8.91; S, 10.14.

EXAMPLE 1

3-Methylamino-4-[3-(3-piperidinomethylphenoxy)-propylamino]-1,2,5-thiadiazole

A.

N-Methyl-N′-[3-(3-piperidinomethylphenoxy)propyl]-ethanediimidamide trihydrochloride A suspension of 3-methylamino-4-[3-(3-piperidinomethylphenoxy)propylamino]-1,2,5-thiadiazole 1-oxide (4.13 g; 10.9 mmoles) [prepared according to the procedure of U.S. Pat. No. 4,374,248] in 100 ml of methanol was treated with 7.2 ml of concentrated HCl. After stirring at ambient temperature for 3 hours, the solution was concentrated and the residue was triturated with acetone, filtered and dried to give 4.35 g (90.4%) of product. A sample was recrystallized from aqueous isopropyl alcohol to give the title compound, mp 207°–225° C. (dec.).

Anal. Calc'd. for $C_{18}H_{29}N_5O.3HCl$: C, 49.03; H, 7.33; N, 15.89. Found (corr. for 0.94% $H_2O$): C, 49.37; H, 7.35; N, 15.71.

B.

3-Methylamino-4-[3-(3-piperidinomethylphenoxy)-propylamino]1,2,5-thiadiazole

A mixture of N-methyl-N′-[3-(3-piperidinomethylphenoxy)propyl]ethanediimidamide trihydrochloride (3.74 g; 8.47 mmoles) [prepared in Step A], 34 ml of $CH_2Cl_2$ and 3.5 ml of triethylamine was treated with N,N′-thiobisphthalimide (DMF solvate) (3.36 g; 8.46 mmoles) and stirred for one hour. The mixture was washed with 30 ml of 10% KOH, dried ($MgSO_4$), filtered, diluted with toluene and concentrated to give 3.6 g of the product. The product was purified by flash chromatography on 90 g of silica gel (230–400 mesh) using ethyl acetate-methanol (95:5) as the eluent to give 1.9 g (62%) of the title compound. Treatment of the product with an equivalent amount of aqueous HCl in 1-propanol gave the hydrochloride salt of the title compound, mp 163.5°–164.5° C.

Anal. Calc'd. for $C_{18}H_{27}N_5OS.HCl$: C, 54.32; H, 7.04; N, 17.60; S, 8.06; Cl, 8.91. Found: C, 54.35; H, 7.07; N, 17.64; S, 8.36; Cl, 8.86.

EXAMPLE 2

3-Benzylamino-4-[3-(3-piperidinomethylphenoxy)-propylamino]-1,2,5-thiadiazole

A.
N-Benzyl-N'-[3-(3-piperidinomethylphenoxy)propyl]ethanediimidamide trihydrochloride A suspension of 3-benzylamino-4-[3-(3-piperidinomethylphenoxy)propylamino]-1,2,5-thiadiazole 1-oxide (5.14 g; 11.3 mmoles) [prepared according to the procedure of U.S. Pat. No. 4,374,248] in 100 ml of methanol was treated with 7.55 ml of concentrated HCl. After stirring at ambient temperature for 3 hours, the solution was concentrated and the residue was triturated with acetone, filtered and dried to give 5.16 g (88%) of the title compound, mp 187°–205° C. (dec.).

Anal. Calc'd. for $C_{24}H_{33}N_5O\cdot 3HCl$: C, 55.75; H, 7.03; N, 13.55; Cl, 20.57. Found: C, 54.88; H, 6.75; N, 13.33; Cl, 20.20.

B.
3-Benzylamino-4-[3-(3-piperidinomethylphenoxy)-propylamino]-1,2,5-thiadiazole A mixture of N-benzyl-N'-[3-(3-piperidinomethylphenoxy)propyl]ethanediimidamide trihydrochloride (4.73 g; 9.16 mmoles) [prepared in Step A], 45 ml of $CH_2Cl_2$ and 3.8 ml of triethylamine was treated with N,N'-thiobisphthalimide (DMF solvate) (3.64 g; 9.16 mmoles) and stirred for one hour. The mixture was washed with 44 ml of 10% KOH, dried ($MgSO_4$), filtered, diluted with toluene and concentrated. The residue was chromatographed by flash chromatography on 110 g of silica gel (230–400 mesh) using ethyl acetate as the eluent to give 3.1 g (77%) of the title compound. Treatment of the product with an equivalent amount of aqueous HCl in 2-propanol gave the hydrochloride salt of the title compound, mp 138°–141° C.

Anal. Calc'd. for $C_{24}H_{31}N_5OS\cdot HCl$: C, 60.80; H, 6.80; N, 14.77; S, 6.76; Cl, 7.48. Found: C, 60.53; H, 6.64; N, 14.99; S, 6.91; Cl, 7.47.

EXAMPLE 3

3-Amino-4-[3-(3-piperidinomethylphenoxy)-propylamino]-1,2,5-thiadiazole

A.
N-[3-(3-Piperidinomethylphenoxy)propyl]ethanediimidamide trihydrochloride A suspension of 3-amino-4-[3-(3-piperidinomethylphenoxy)propylamino]-1,2,5-thiadiazole 1-oxide (17.1 g; 47.0 mmoles) [prepared according to the procedure of U.S. Pat. No. 4,374,248] in 450 ml of methanol was treated with 38 mL of concentrated HCl. The resultant solution was stirred for 3 hours at ambient temperature. Concentration of the solution followed by azeotropic removal of water with absolute ethanol gave colorless crystals. These were suspended in 200 mL of absolute ethanol, filtered and dried under vacuum to give 16.6 g (82.6%) of the title compound, m.p. 205°–222° C. (dec.). Recrystallization from 50% methanolethyl acetate gave an analytical sample, m.p. 206°–216° C. (dec.).

Anal. Calc'd for $C_{17}H_{27}N_5O\cdot 3HCl$: C, 47.84; H, 7.08; N, 16.41. Found: C, 47.56; H, 7.18; N, 16.75.

B.
3-Amino-4-[3-(3-piperidinomethylphenoxy)-propylamino]-1,2,5-thiadiazole A mixture of N-[3-(3-piperidinomethylphenoxy)propyl]-ethanediimidamide trihydrochloride (27.3 g; 64.0 mmoles) [prepared in Step A], 250 ml of $CH_2Cl_2$ and 26.6 ml (192.0 mmoles) of triethylamine was treated portionwise with N,N'-thiobisphthalimide (DMF solvate) (25.4 g; 64.0 mmoles). After stirring at ambient temperature for one hour, the mixture was washed with 120 ml of 20% KOH, dried ($MgSO_4$), filtered and concentrated, then taken up in 150 ml of toluene and reconcentrated. The product was taken up in 250 ml of 1-propanol and 10.7 ml of 6 N HCl, treated with decolorizing carbon and filtered through Celite. This solution was concentrated to 100 ml volume, diluted with 175 ml of dry 1-propanol and stored at 0° C. to give 20.2 g (82.1%) of crystalline hydrochloride salt of the title compound, mp 137°–138° C.

Anal. Calc'd. for $C_{17}H_{25}N_5OS\cdot HCl$: C, 53.18; H, 6.83; N, 18.24; S, 8.35. Found: C, 52.78; H, 6.74; N, 18.52; S, 8.66.

EXAMPLE 4

3-Amino-4-[3-(3-pyrrolidinomethylphenoxy)-propylamino]-1,2,5-thiadiazole

A.
N-[3-(3-Pyrrolidinomethylphenoxy)propyl]ethanediimidamide trihydrochloride A suspension of 3-amino-4-[3-(3-pyrrolidinomethylphenoxy)propylamino]-1,2,5-thiadiazole 1-oxide (13.4 g; 38.3 mmoles) [prepared according to the procedure of U.S. Pat. No. 4,374,248] in 350 ml of methanol was treated with 25.5 mL of concentrated HCl. The resultant solution was stirred for 3 hours at ambiet temperature. Concentration of the solution followed by azeotropic removal of water with absolute ethanol gave the product. The crystalline residue was triturated with 150 mL of absolute ethanol, filtered and dried to give 10.8 g of the title compound, m.p. 195°–203° C. (dec.).

Anal. Calc'd for $C_{16}H_{25}N_5O\cdot 3HCl$: C, 46.55; H, 6.84; N, 16.97. Found: C, 46.55; H, 6.93; N, 16.93.

B.
3-Amino-4-[3-(3-pyrrolidinomethylphenoxy)-propylamino]-1,2,5-thiadiazole A mixture of N-[3-(3-pyrrolidinomethylphenoxy)propyl]-ethanediimidamide trihydrochloride (22.0 g; 53.0 mmoles) [prepared in Example 4, Step A], 200 ml of $CH_2Cl_2$ and 22 ml of triethylamine was treated with N,N'-thiobisphthalimide (DMF solvate) (21.2 g; 53.0 mmoles). After stirring at ambient temperature for one hour, the mixture was washed with 100 ml of 20% KOH, dried ($MgSO_4$), filtered, diluted with 100 ml of toluene and concentrated. The product was treated with one equivalent of aqueous HCl in 1-propanol to give 13.2 g (67%) of the hydrochloride salt of the title compound, mp 135°–137° C.

Anal. Calc'd for $C_{16}H_{23}N_5OS\cdot HCl$: C, 51.95; H, 6.54; N, 18.93; S, 8.67. Found: C, 51.92; H, 6.55; N, 19.30; S, 9.06.

EXAMPLE 5

3-Amino-4-{2-[(5-dimethylaminomethyl-3-thienyl)methylthio]-ethylamino}-1,2,5-thiadiazole

A.
N-{2-[(5-dimethylaminomethyl-3-thienyl)methylthio]ethyl}-ethanediimidamide trihydrochloride A suspension of 3-amino-4-{2-[(5-dimethylaminomethyl-3-thienyl)methylthio]ethylamino}-1,2,5-thiadiazole 1-oxide (7.8 g; 22.6 mmoles) [prepared according to the procedure of U.S. Pat. No. 4,374,248] in 150 ml of methanol was treated with 15.0 ml of concentrated HCl. After stirring at ambient temperature for 3 hours, the solution was concentrated and the residue triturated with 1-propanol, filtered and dried to give 7.38 g (80%) of product. A sample was recrystallized from methanol-acetone to give the title compound, mp 190°–205° C. (dec.).

Anal. Calc'd. for $C_{12}N_{21}N_5S_2.3HCl$: C, 35.25; H, 5.92; N, 17.13. Found: C, 35.03; H, 5.93; N, 17.39.

B.
3-Amino-4-{2-[(5-dimethylaminomethyl-3-thienyl)methylthio]-ethylamino}-1,2,5-thiadiazole A mixture of N-{2-[(5-dimethylaminomethyl-3-thienyl)-methylthio]ethyl}ethanediimidamide trihydrochloride (6.13 g; 15.0 mmoles) [prepared in Step A], 60 ml of $CH_2Cl_2$ and 6.3 ml of triethylamine was treated with N,N'-thiobisphthalimide (DMF solvate) (5.96 g; 15.0 mmoles) and stirred for one hour. The mixture was washed with 100 ml of 10% KOH, dried ($MgSO_4$), filtered, diluted with toluene and concentrated to give 5.1 g of product. Treatment of the product with 0.5 molar equivalent of fumaric acid in 1-propanol gave the fumaric acid salt of the compound, mp 141°–143° C. The nmr spectrum in DMSO-$d_6$ shows the presence of approximately 0.12 moles of 1-propanol.

Anal. Calc'd. for $(C_{12}H_{19}N_5S_3)_2.C_4H_4O_4.0.12C_3H_8O$: C, 43.68; H, 5.61; N, 17.75; S, 24.38. Found: C, 43.41; H, 5.53; N, 17.54; S, 24.24.

EXAMPLE 6

3-Amino-4-{2-[(5-piperidinomethyl-3-thienyl)methylthio]ethylamino}-1,2,5-thiadiazole

A.
N-{2-[(5-piperidinomethyl-3-thienyl)methylthio]ethyl}ethanediimidamide trihydrochloride A suspension of 3-amino-4-{2-[(5-piperidinomethyl-3-thienyl)methylthio]ethylamino}-1,2,5-thiadiazole 1-oxide (6.1 g; 15.8 mmoles) [prepared according to the procedure of U.S. Pat. No. 4,374,248] in 80 ml of methanol was treated with 10.5 ml of concentrated HCl. After stirring at ambient temperature for 3 hours, the solution was concentrated and the residue triturated with 50 ml of 1-propanol, filtered and dried to give 5.86 g (83%) of product. A sample was recrystallized from methanol-acetone to give the title compound, mp 201°–214° C. (dec.).

Anal. Calc'd. for $C_{15}H_{25}N_5S_2.3HCl$: C, 40.13; H, 6.29; N, 15.60; S, 14.29. Found: C, 39.97; H, 6.47; N, 15.28; S, 14.63.

B.
3-Amino-4-{2-[(5-piperidinomethyl-3-thienyl)methylthio]-ethylamino}-1,2,5-thiadiazole A mixture of N-{2-[(5-piperidinomethyl-3-thienyl)-methylthio]ethyl}ethanediimidamide trihydrochloride (5.17 g; 11.5 mmoles) [prepared in Step A], 48 ml of $CH_2Cl_2$ and 4.8 ml of triethylamine was treated with N,N'-thiobisphthalimide (DMF solvate) (4.57 g; 11.5 mmoles) and stirred for one hour. The mixture was washed with 90 ml of 10% KOH, dried ($MgSO_4$), filtered, diluted with toluene and concentrated to give 4.5 g of product. Treatment of the product with one equivalent of cyclohexyl sulfamic acid in methanol gave the cyclohexyl sulfamate salt of the title compound, mp 142°–143° C.

Anal. Calc'd. for $C_{15}H_{23}N_5S_3.C_6H_{13}NO_3S$: C, 45.96; H, 6.61; N, 15.31; S, 23.38. Found: C, 45.61; H, 6.41; N, 15.46; S, 23.48.

EXAMPLE 7

3-Amino-4-[3-(6-piperidinomethyl-2-pyridyloxy)-propylamino]-1,2,5-thiadiazole

A.
3-Amino-4-[3-(6-piperidinomethyl-2-pyridyloxy)-propylamino]-1,2,5-thiadiazole 1-oxide A solution of 3-(6-piperidinomethyl-2-pyridyloxy)-propylamine (4.65 g; 18.6 mmoles) [prepared according to published U.K. patent application No. 2,098,988] in 50 ml of methanol was reacted with 3-amino-4-methoxy-1,2,5-thiadiazole 1-oxide (2.74 g; 18.6 mmoles) according to the general procedure described in U.S. Pat. No. 4,374,248 to give a solution containing 3-amino-4-[3-(6-piperidinomethyl-2-pyridyloxy)-propylamino]-1,2,5-thiadiazole 1-oxide. A purified sample melted at 145°–147° C.

B.
N-[3-(6-Piperidinomethyl-2-pyridyloxy)propyl]ethanediimidamide trihydrochloride A methanolic solution of the product prepared in Step A was diluted to 100 ml and 12.4 ml of concentrated HCl was added. The solution was stirred at ambient temperature for 18 hours, concentrated, and the residue was dissolved in 80 ml of water and extracted twice with $CH_2Cl_2$. The aqueous layer was concentrated, treated with n-propanol and concentrated under high vacuum to give the title compound as a foam.

C.
3-Amino-4-[3-(6-piperidinomethyl-2-pyridyloxy)-propylamino]-1,2,5-thiadiazole A mixture of the crude product prepared in Step B in 80 ml of $CH_2Cl_2$ and containing 7.69 ml of triethylamine was treated with N,N'-thiobisphthalimide (DMF solvate) (7.35 g; 18.5 mmoles). After stirring at ambient temperature for one hour, the mixture was washed with 50 ml of 4 N NaOH, water, saturated aqueous NaCl solution, dried ($Na_2SO_4$), filtered and evaporated under reduced pressure to give the crude product. The product was purified by flash chromatography on 100 g of silica gel (230–400 mesh) using ethyl acetate-methanol (95:5) as the eluent to give 3.63 g of the title compound as a viscous oil. Treatment of the product with one equivalent of cyclohexyl sulfamic acid in acetone gave the cyclohexyl sulfamate salt of the title compound, mp 125.5°–131° C.

Anal. Calc'd. for $C_{16}H_{24}N_6OS$ $C_6H_{13}NO_3S$: C, 50.07; H, 7.07; N, 18.58; S, 12.15. Found: C, 50.02; H, 7.03; N, 18.54; S, 12.14.

EXAMPLE 8

3-Amino-4-[3-(4-piperidinomethyl-2-pyridyloxy)-propylamino]-1,2,5-thiadiazole

A. 3-(4-Piperidinomethyl-2-pyridyloxy)propylamine

When the general procedure for the preparation of 3-(6-piperidinomethyl-2-pyridyloxy)propylamine described in U.K. Patent Application No. 2,098,988 was followed except that the 2-chloro-6-methylpyridine utilized therein was replaced by 2-bromo-4-methylpyridine, then the title compound was produced as an oil.

Anal. Calc'd. for $C_{14}H_{23}N_3O$: C, 67.44; H, 9.30; N, 16.85. Found: C, 67.54; H, 8.98; N, 16.55.

B.

3-Amino-4-[3-(4-piperidinomethyl-2-pyridyloxy)-propylamino]-1,2,5-thiadiazole 1-oxide A solution of the product of Step A (6.5 g; 26.0 mmoles) in 90 ml of methanol was reacted with 3-amino-4-methoxy-1,2,5-thiadiazole 1-oxide (3.84 g; 26.0 mmoles) according to the general procedures described in U.S. Pat. No. 4,374,248 to give 6.33 g of product. Recrystallization from methanolacetonitrile yielded the title compound, mp 154°–158° C.

Anal. Calc'd. for $C_{16}H_{24}N_6OS$: C, 52.73; H, 6.64; N, 23.06; S, 8.80. Found: C, 52.72; H, 6.30; N, 23.32; S, 8.74.

C.

N-[3-(4-Piperidinomethyl-2-pyridyloxy)propyl]ethanediimidamide trihydrochloride

The product of Step B (5.0 g; 13.7 mmoles) was dissolved in 80 ml of methanol and treated with 9.1 ml of concentrated HCl. After stirring at ambient temperature for 4.5 hours, the solution was evaporated to dryness under reduced pressure to give the title compound.

D.

3-Amino-4-[3-(4-piperidinomethyl-2-pyridyloxy)-propylamino]-1,2,5-thiadiazole

A mixture of the product prepared in Step C in 50 ml of $CH_2Cl_2$ and 5.7 ml of triethylamine was treated with N,N'-thiobisphthalimide (DMF solvate) (5.44 g; 13.7 mmoles). After stirring at ambient temperature for one hour, the mixture was washed with 40 ml of 4 N NaOH, water, saturated aqueous NaCl solution, dried ($Na_2SO_4$), filtered and evaporated under reduced pressure to give the crude product. The product was purified by flash chromatography on 90 g of silica gel (230–400 mesh) using ethyl acetate-methanol (96:4) as the eluent to give 3.44 g of the title compound as a viscous oil. Treatment of the product with one equivalent of cyclohexyl sulfamic acid in acetone gave the cyclohexyl sulfamate of the title compound, mp 124.5°–126° C.

Anal. Calc'd. for $C_{16}H_{24}N_6OS \cdot C_6H_{13}NO_3S$: C, 50.07; H, 7.07; N, 18.58; S, 12.15. Found: C, 50.47; H, 7.12; N, 18.33; S, 11.87.

EXAMPLE 9

3-Amino-4-{3-[3-(1,2,3,6-tetrahydro-1-pyridyl)methylphenoxy]-propylamino}-1,2,5-thiadiazole The general procedure of Example 8 was repeated, except that the 3-(6-piperidinomethyl-2-pyridyloxy)-propylamine utilized therein was replaced by an equivalent amount of 3-[3-(1,2,3,6-tetrahydro-1-pyridyl)methylphenoxy]propylamine, to give 2.31 g of product. Crystallization from toluene yielded the title compound, mp 99.5°–104° C.

Anal. Calc'd. for $C_{17}N_{23}N_5OS$: C, 59.10; H, 6.71; N, 20.27; S, 9.28. Found (corr. for 2.19% $H_2O$): C, 58.78; H, 6.71; N, 19.90; S, 9.26.

EXAMPLE 10

3-Amino-4-{2-[(5-dimethylaminomethyl-2-furyl)methylthio]ethyl-amino}-1,2,5-thiadiazole The general procedure of Example 5 is repeated except that the 3-amino-4-{2-[(5-dimethylaminomethyl-3-thienyl)methylthio]ethylamino}-1,2,5-thiadiazole 1-oxide utilized therein is replaced by an equimolar amount of 3-amino-4-{2-[(5-dimethylaminomethyl-2-furyl)methylthio]ethylamino}-1,2,5-thiadiazole 1-oxide [prepared according to U.S. Pat. No. 4,374,248], and the title compound is thereby produced. Treatment of a portion of the product with an equivalent amount of 2 N HCl in methanol produces the hydrochloride salt of the title compound.

Treatment of another portion of the product with an equivalent amount of cyclohexylsulfamic acid in acetone produces the cyclohexylsulfamate salt of the title compound.

EXAMPLE 11

3-Amino-4-{2-[(5-dimethylaminomethyl-4-methyl-2-thienyl)methylthio]ethylamino}-1,2,5-thiadiazole The general procedure of Example 5 is repeated except that the 3-amino-4-{2-[(5-dimethylaminomethyl-3-thienyl)methylthio]ethylamino}-1,2,5-thiadiazole 1-oxide utilized therein is replaced by an equimolar amount of 3-amino-4-{2-[(5-dimethylaminomethyl-4-methyl-2-thienyl)methylthio]ethylamino}-1,2,5-thiadiazole 1-oxide [prepared according to the general procedure described in U.S. Pat. No. 4,374,248], and the title compound is thereby produced.

EXAMPLE 12

The general procedure of Example 3 is repeated except that the 3-amino-4-[3-(3-piperidinomethylphenoxy)propylamino]-1,2,5-thiadiazole 1-oxide utilized therein is replaced by an equimolar amount of (a) 3-amino-4-[3-(3-dimethylaminomethylphenoxy)-propylamino]-1,2,5-thiadiazole 1-oxide, (b) 3-amino-4-[3-(3-diethylaminomethylphenoxy)-propylamino]-1,2,5-thiadiazole 1-oxide, (c) 3-amino-4-{3-[3-(2-methylpyrrolidino)methylphenoxy]-propylamino}-1,2,5-thiadiazole 1-oxide, (d) 3-amino-4-{3-[3-(3-methylpyrrolidino)methylphenoxy]-propylamino}-1,2,5-thiadiazole 1-oxide, (e) 3-amino-4-}3-[3-(4-methylpiperidino)methylphenoxy]-propylamino}-1,2,5-thiadiazole 1-oxide, (f) 3-amino-4-[3-(3-morpholinomethylphenoxy)-propylamino]-1,2,5-thiadiazole 1-oxide, (g) 3-amino-4-{3-[3-(N-methylpiperazino)methylphenoxy]-propylamino}-1,2,5-thiadiazole 1-oxide, (h) 3-amino-4-[3-(3-diallylaminomethylphenoxy)-propylamino]-1,2,5-thiadiazole 1-oxide, (i) 3-amino-4-[3-(3-hexamethyleneiminomethylphenoxy)propylamino]-1,2,5-thiadiazole 1-oxide, (j) 3-amino-4-[3-(3-heptamethyleneiminomethylphenoxy)propylamino]-1,2,5-thiadiazole 1-oxide, (k) 3-amino-4-{3-[3-(3-azabicyclo[3.2.2]non-3-yl)methylphenoxy]-propylamino}-1,2,5-thiadiazole 1-oxide and (l) 3-amino-4-{3-[3-(3-pyrrolino)methylphenoxy]-propylamino}-1,2,5-thiadiazole 1-oxide, respectively, each of which is prepared by the general procedure of U.S. Pat. No. 4,374,248, and there is thereby produced
(a) 3-amino-4-[3-(3-dimethylaminomethylphenoxy)-propylamino]-1,2,5-thiadiazole,
(b) 3-amino-4-[3-(3-diethylaminomethylphenoxy)-propylamino]-1,2,5-thiadiazole,
(c) 3-amino-4-{3-[3-(2-methylpyrrolidino)methylphenoxy]-propylamino}-1,2,5-thiadiazole,
(d) 3-amino-4-{3-[3-(3-methylpyrrolidino)methylphenoxy]-propylamino}-1,2,5-thiadiazole,
(e) 3-amino-4-{3-[3-(4-methylpiperidino)methylphenoxy]-propylamino}-1,2,5-thiadiazole,
(f) 3-amino-4-[3-(3-morpholinomethylphenoxy)-propylamino]-1,2,5-thiadiazole,
(g) 3-amino-4-{3-[3-(N-methylpiperazino)methylphenoxy]-propylamino}-1,2,5-thiadiazole,
(h) 3-amino-4-[3-(3-diallylaminomethylphenoxy)-propylamino]-1,2,5-thiadiazole,
(i) 3-amino-4-[3-(3-hexamethyleneiminomethylphenoxy)propylamino]-1,2,5-thiadiazole,
(j) 3-amino-4-[3-(3-heptamethyleneiminomethylphenoxy)propylamino]-1,2,5-thiadiazole,
(k) 3-amino-4-{3-[3-(3-azabicyclo[3.2.2.]non-3-yl)methylphenoxy]-propylamino}-1,2,5-thiadiazole and
(l) 3-amino-4-{3-[3-(3-pyrrolino)methylphenoxy]-propylamino}-1,2,5-thiadiazole, respectively.

EXAMPLE 13

The general procedure of Example 3 is repeated except that the 3-amino-4-[3-(3-piperidinomethylphenoxy)propylamino]-1,2,5-thiadiazole 1-oxide utilized therein is replaced by an equimolar amount of
(a) 3-ethylamino-4-[3-(3-piperidinomethylphenoxy)-propylamino]-1,2,5-thiadiazole 1-oxide,
(b) 3-allylamino-4-[3-(3-piperidinomethylphenoxy)-propylamino]-1,2,5-thiadiazole 1-oxide,
(c) 3-(2-propynyl)-4-[3-(3-piperidinomethylphenoxy)-propylamino]-1,2,5-thiadiazole 1-oxide,
(d) 3-(3-pyridylmethylamino)-4-[3-(3-piperidinomethylphenoxy)-propylamino]-1,2,5-thiadiazole 1-oxide,
(e) 3-(6-methyl-3-pyridyl)methylamino-4-[3-(3-piperidinomethylphenoxy)propylamino]-1,2,5-thiadiazole 1-oxide and
(f) 3-(3,4-methylenedioxybenzylamino)-4-[3-(3-piperidinomethylphenoxy)propylamino]-1,2,5-thiadiazole 1-oxide, respectively,
each of which is prepared by the general procedure of U.S. Pat. No. 4,374,248, and there is thereby produced
(a) 3-ethylamino-4-[3-(3-piperidinomethylphenoxy)-propylamino]-1,2,5-thiadiazole,
(b) 3-allylamino-4-[3-(3-piperidinomethylphenoxy)-propylamino]-1,2,5-thiadiazole,
(c) 3-(2-propynyl)-4-[3-(3-piperidinomethylphenoxy)-propylamino]-1,2,5-thiadiazole,
(d) 3-(3-pyridylmethylamino)-4-[3-(3-piperidinomethylphenoxy)-propylamino]-1,2,5-thiadiazole,
(e) 3-(6-methyl-3-pyridyl)methylamino-4-[3-(3-piperidinomethylphenoxy)propylamino]-1,2,5-thiadiazole and
(f) 3-(3,4-methylenedioxybenzylamino)-4-[3-(3-piperidinomethylphenoxy)propylamino]-1,2,5-thiadiazole, respectively.

EXAMPLE 14

3-Amino-4-[3-(6-dimethylaminomethyl-2-pyridyloxy)-propylamino]-1,2,5-thiadiazole When a methanolic solution of 3-(6-dimethylaminomethyl-2-pyridyloxy)propylamine [prepared according to published United Kingdom Patent Application No. 2,098,988] is reacted with 3-amino-4-methoxy-1,2,5-thiadiazole 1-oxide according to the general procedure described in U.S. Pat. No. 4,374,248, and the resulting 3-amino-4-[3-(6-piperidinomethyl-2-pyridyloxy)-propylamino]-1,2,5-thiadiazole 1-oxide is reacted according to the general procedure described in Example 3, the title compound is thereby produced.

EXAMPLE 15

3-Amino-4-{2-[(6-dimethylaminomethyl-2-pyridyl)methylthio]-ethylamino}-1,2,5-thiadiazole When a suspension of 3-amino-4-{2-[(6-dimethylaminomethyl-2-pyridyl)methylthio]ethylamino}-1,2,5-thiadiazole 1-oxide [prepared according to U.S. Pat. No. 4,374,248] is reacted according to the procedure of Example 3, the title compound is thereby produced.

EXAMPLE 16

3-Amino-4-{2-[(6-piperidinomethyl-2-pyridyl)methylthio]ethylamino}-1,2,5-thiadiazole When a suspension of 3-amino-4-{2-[(6-piperidinomethyl-2-pyridyl)methylthio]ethylamino}-1,2,5-thiadiazole 1-oxide [prepared according to U.S. Pat. No. 4,374,248] is reacted according to the procedure of Example 3, the title compound is thereby produced.

EXAMPLE 17

The general procedure of Example 3 is repeated except that the 3-amino-4-[3-(3-piperidinomethylphenoxy)propylamino]-1,2,5-thiadiazole 1-oxide utilized therein is replaced by an equimolar amount of
(a) 3-amino-4-[3-(3-piperidinomethylthiophenoxy)-propylamino]-1,2,5-thiadiazole 1-oxide,
(b) 3-amino-4-[3-(3-dimethylaminomethylthiophenoxy)-propylamino]-1,2,5-thiadiazole 1-oxide,
(c) 3-amino-4-[3-(3-pyrrolidinomethylthiophenoxy)-propylamino]-1,2,5-thiadiazole 1-oxide,
(d) 3-amino-4-[3-(4-dimethylaminomethyl-2-pyridyloxy)-propylamino]-1,2,5-thiadiazole 1-oxide,
(e) 3-amino-4-[3-(5-dimethylaminomethyl-3-thienyloxy)propylamino]-1,2,5-thiadiazole 1-oxide,
(f) 3-amino-4-[3-(5-piperidinomethyl-3-thienyloxy)-propylamino]-1,2,5-thiadiazole 1-oxide,
(g) 3-amino-4-{2-[(4-dimethylaminomethyl-2-pyridyl)-methylthio]-ethylamino}-1,2,5-thiadiazole 1-oxide and
(h) 3-amino-4-{2-[(4-piperidinomethyl-2-pyridyl)methylthio]-ethylamino}-1,2,5-thiadiazole 1-oxide, respectively,
each of which is prepared by the general procedure of U.S. Pat. No. 4,374,248, and there is thereby produced
(a) 3-amino-4-[3-(3-piperidinomethylthiophenoxy)-propylamino]-1,2,5-thiadiazole,
(b) 3-amino-4-[3-(3-dimethylaminomethylthiophenoxy)-propylamino]-1,2,5-thiadiazole,
(c) 3-amino-4-[3-(3-pyrrolidinomethylthiophenoxy)-propylamino]-1,2,5-thiadiazole, d) 3-amino-4-[3-(4-dimethylaminomethyl-2-pyridyloxy)-propylamino]-1,2,5-thiadiazole,
e) 3-amino-4-[3-(5-dimethylaminomethyl-3-thienyloxy)propylamino]-1,2,5-thiadiazole,
f) 3-amino-4-[3-(5-piperidinomethyl-3-thienyloxy)-propylamino]-1,2,5-thiadiazole,
g) 3-amino-4-{2-[(4-dimethylaminomethyl-2-pyridyl)-methylthio]-ethylamino}-1,2,5-thiadiazole and
h) 3-amino-4-{2-[(4-piperidinomethyl-2-pyridyl)methylthio]-ethylamino}-1,2,5-thiadiazole, respectively.

EXAMPLE 18

3-Amino-4-[3-(3-piperidinomethylphenoxy)-propylamino]-1,2,5-thiadiazole

The general procedure of Example 3 is repeated, except that the N,N'-thiobisphthalimide utilized therein is replaced by an equimolar amount of
N,N'-thiobis-4-chlorophthalimide,
N,N'-thiobis-4,5-dichlorophthalimide,
N,N'-thiobis-3-nitrophthalimide,
N,N'-thiobis-4-nitrophthalimide,
N,N'-thiobissuccinimide,
N,N'-thiobis-2,3-dimethylsuccinimide,
N,N'-thiobis-2-methylsuccinimide,
N,N'-thiobis-2-phenylsuccinimide,
N,N'-thiobismaleimide,
N,N'-thiobis-2,3-dimethylmaleimide,
1,1'-thiobisimidazole,
1,1'-thiobis(1,2,4-triazole),
1,1'-thiobis(1,2,3-benzotriazole),
1,1'-thiobis-5-chlorobenzotriazole,
1,1'-thiobis-5,6-dimethylbenzotriazole,
1,1'-thiobisbenzimidazole,
1,1'-thiobis-5-chlorobenzimidazole,
1,1'-thiobis-5-methylbenzimidazole,
1,1'-thiobis-5,6-dichlorobenzimidazole,
1,1'-thiobis-5,6-dimethylbenzimidazole,
1,1'-thiobis-5-methoxybenzimidazole,
1,1'-thiobis-5-nitrobenzimidazole, pyrazole,
3,5-dimethylpyrazole and
3,3'-thiobis(5,5-dimethylhydantoin), respectively,
and in each case 3-amino-4-[3-(3-piperidinomethylphenoxy)propylamino]-1,2,5-thiadiazole is thereby produced.

I claim:
1. A process for the preparation of a compound of the formula

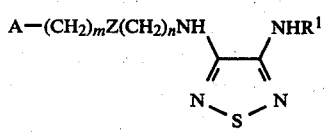

wherein R¹ is hydrogen, (lower)alkyl, 2-fluoroethyl, 2,2,2-trifluoroethyl, allyl, propargyl,

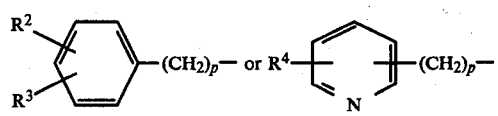

in which
p is 1 or 2, R² and R³ each are independently hydrogen, (lower)alkyl, (lower)alkoxy or halogen, and, when R² is hydrogen, R³ also may be trifluoromethyl, or R² and R³, taken together, may be methylenedioxy, and R⁴ is hydrogen, (lower)alkyl or (lower)alkoxy;
m is an integer of from 0 to 2 inclusive;
n is an integer of from 2 to 5 inclusive;
Z is oxygen, sulfur or methylene; and
A is

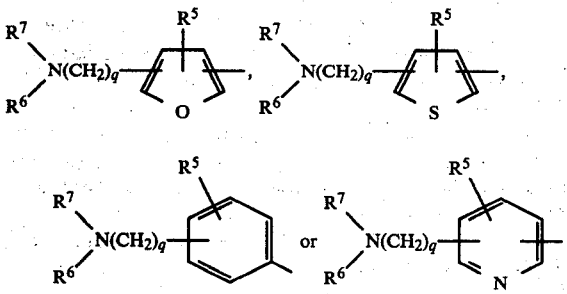

in which R⁵ is hydrogen, (lower)alkyl or (lower)alkoxy, q is an integer of from 1 to 4 inclusive and R⁶ and R⁷ each are independently (lower)alkyl, (lower)alkoxy(lower)alkyl in which the (lower)alkoxy moiety is at least two carbon atoms removed from the nitrogen atom, or phenyl(lower)alkyl, and, when R⁶ is hydrogen, R⁷ also may be cyclo(lower)alkyl, or R⁶ and R⁷, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, 3-azabicyclo[3.2.2]non-3-yl or 3-pyrrolino; and nontoxic, pharmaceutically acceptable salts, hydrates and solvates thereof; which process comprises reacting a substituted ethanediimidamide of the formula

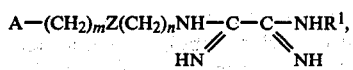

in which A, m, Z, n and R¹ are as described above, with a compound of the formula

R—S—R  VII in which the two R groups are the same and may be

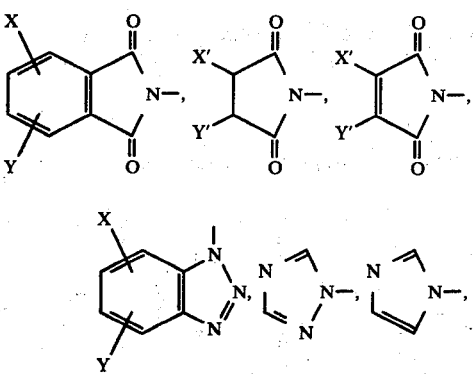

-continued

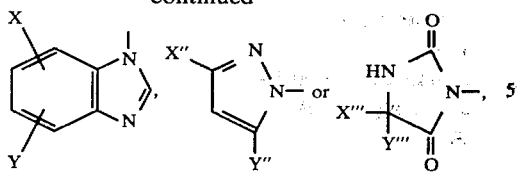

in which X and Y are independently hydrogen, (lower-)alkyl, (lower)alkoxy, chloro, bromo, nitro, methanesulfonyl, benzenesulfonyl, cyclo(lower)alkyl or phenyl, X' and Y' are independently hydrogen, (lower)alkyl or phenyl, X'' and Y'' are independently hydrogen or (lower)alkyl and X''' and Y''' are independently (lower)alkyl or phenyl, in a non-reactive organic solvent, at a temperature of from about 0° C. to about 100° C.

2. A process of claim 1 for the preparation of a compound of the formula

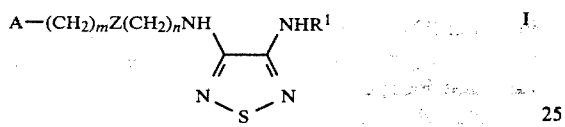

wherein $R^1$ is hydrogen or (lower)alkyl, m is 0 or 1, n is 2 or 3, Z is oxygen or sulfur and A is

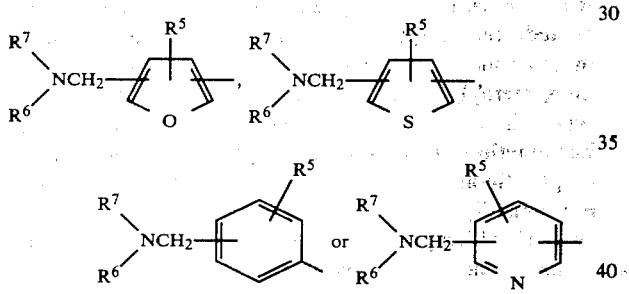

in which $R^5$ is hydrogen or methyl, and $R^6$ and $R^7$ each are independently methyl or ethyl, or when taken together with the nitrogen to which they are attached, $R^6$ and $R^7$ represent a pyrrolidino or piperidino ring; or a nontoxic pharmaceutically acceptable salt, hydrate or solvate thereof; which process comprises reacting a substituted ethanediimidamide of the formula

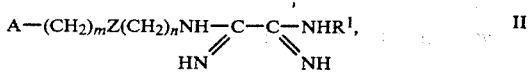

in which A, m, Z, n and $R^1$ are as described above, with a compound of the formula

R—S—R    VII in which the two R groups are the same and may be

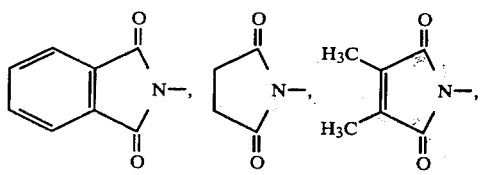

-continued

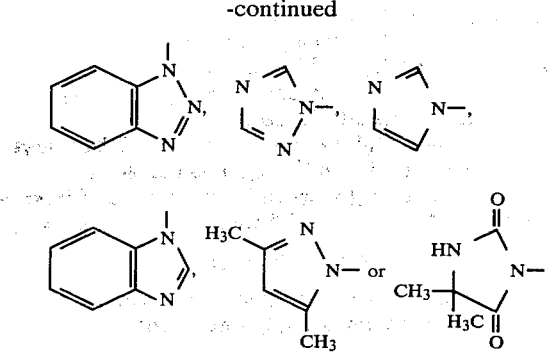

in a non-reactive organic solvent, at a temperature of from about 0° C. to about 100° C.

3. A process of claim 1 for the preparation of a compound of the formula

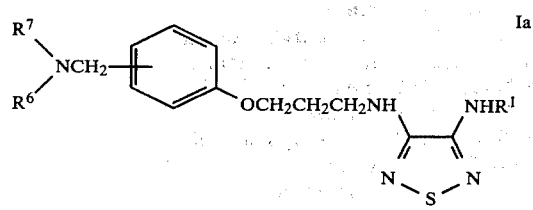

wherein $R^1$ is hydrogen or methyl, and $R^6$ and $R^7$ each are methyl or, when taken together with the nitrogen atom to which they are attached, $R^6$ and $R^7$ represent a pyrrolidino or piperidino ring; or a nontoxic pharmaceutically acceptable salt, hydrate or solvate thereof; which process comprises reacting a compound of the formula

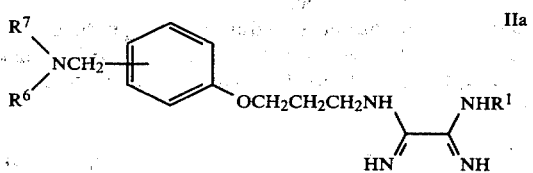

in which $R^1$, $R^6$ and $R^7$ are as defined above, with N,N'-thiobisphthalimide in a non-reactive organic solvent at a temperature of from about 10° C. to about 50° C.

4. A process of claim 1 for the preparation of a compound of the formula

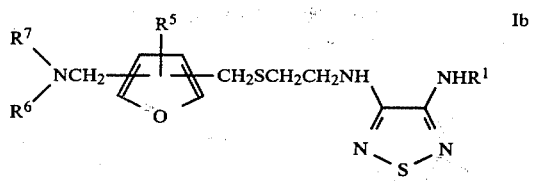

wherein $R^1$ and $R^5$ each are independently hydrogen or methyl, and $R^6$ and $R^7$ each are independently methyl or ethyl; or a nontoxic pharmaceutically acceptable salt, hydrate or solvate thereof; which process comprises reacting a compound of the formula

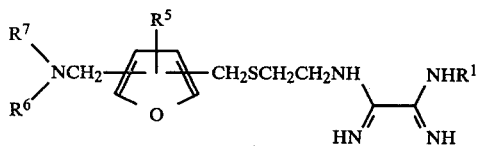

in which $R^1$, $R^5$, $R^6$ and $R^7$ are as defined above, with N,N'-thiobisphthalimide in a non-reactive organic solvent at a temperature of from about 10° C. to about 50° C.

5. A process of claim 1 for the preparation of a compound of the formula

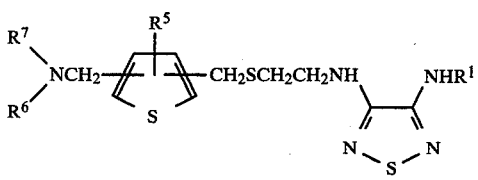

wherein $R^1$ and $R^5$ each are independently hydrogen or methyl, and $R^6$ and $R^7$ each are independently methyl or ethyl; or a nontoxic pharmaceutically acceptable salt, hydrate or solvate thereof; which process comprises reacting a compound of the formula

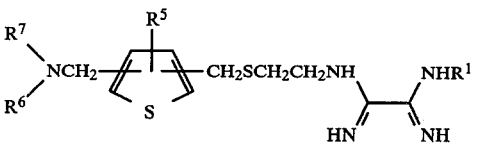

in which $R^1$, $R^5$, $R^6$ and $R^7$ are as defined above, with N,N'-thiobisphthalimide in a non-reactive organic solvent at a temperature of from about 10° C. to about 50° C.

6. A process of claim 1 for the preparation of a compound of the formula

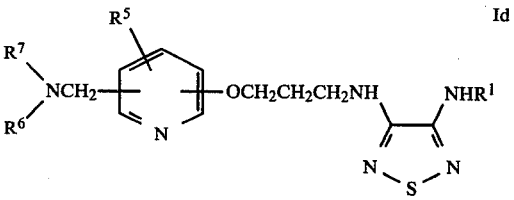

wherein $R^1$ and $R^5$ each are independently hydrogen or methyl, and $R^6$ and $R^7$ each are independently methyl or ethyl, or, when taken together with the nitrogen to which they are attached, $R^6$ and $R^7$ represent piperidino; or a nontoxic pharmaceutically acceptable salt, hydrate or solvate thereof; which process comprises reacting a compound of the formula

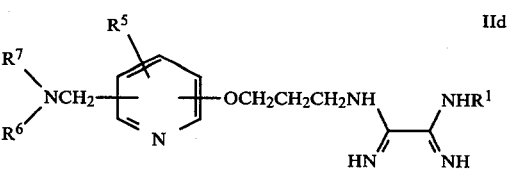

in which $R^1$, $R^5$, $R^6$ and $R^7$ are as defined above, with N,N'-thiobisphthalimide in a non-reactive organic solvent at a temperature of from about 10° C. to about 50° C.

7. A process for the preparation of 3-amino-4-[3-(3-piperidinomethylphenoxy)propylamino]-1,2,5-thiadiazole, or a nontoxic pharmaceutically acceptable salt, hydrate or solvate thereof, which comprises reacting N-[3-(3-piperidinomethylphenoxy)-propyl]ethanediimidamide with about an equimolar amount of N,N'-thiobisphthalimide in a non-reactive organic solvent at a temperature of from about 10° C. to about 50° C.

8. A process for the preparation of 3-amino-4-[3-(3-pyrrolidinomethylphenoxy)propylamino]-1,2,5-thiadiazole, or a nontoxic pharmaceutically acceptable salt, hydrate or solvate thereof, which comprises reacting N-[3-(3-pyrrolidinomethylphenoxy)propyl]ethanediimidamide with about an equimolar amount of N,N'-thiobisphthalimide in a non-reactive organic solvent at a temperature of from about 10° C. to about 50° C.

9. A process for the preparation of 3-amino-4-[3-(4-piperidinomethyl-2-pyridyloxy)propylamino]-1,2,5-thiadiazole, or a nontoxic pharmaceutically acceptable salt, hydrate or solvate thereof, which comprises reacting N-[3-(4-piperidinomethyl-2-pyridyloxy)propyl]ethanediimidamide with about an equimolar amount of N,N'-thiobisphthalimide in a non-reactive organic solvent at a temperature of from about 10° C. to about 50° C.

* * * * *